(12) United States Patent
Singh

(10) Patent No.: US 6,287,602 B1
(45) Date of Patent: Sep. 11, 2001

(54) TREATMENT OF ONCOLOGIC TUMORS WITH AN INJECTABLE FORMULATION OF A GOLGI APPARATUS DISTURBING AGENT

(75) Inventor: Saira Sayed Singh, Los Gatos, CA (US)

(73) Assignee: OncoPharmaceutical, Inc., Morgan Hill (CA)

( * ) Notice: Subject to any disclaimer, the term of this patent is extended or adjusted under 35 U.S.C. 154(b) by 0 days.

(21) Appl. No.: 09/397,390

(22) Filed: Sep. 15, 1999

Related U.S. Application Data

(60) Provisional application No. 60/100,479, filed on Sep. 16, 1998.

(51) Int. Cl.[7] .................................................... A61K 9/14
(52) U.S. Cl. ........................ 424/488; 424/485; 514/449
(58) Field of Search ................................. 514/449, 560, 514/777, 782, 781; 424/488, 485

(56) References Cited

U.S. PATENT DOCUMENTS

| | | |
|---|---|---|
| 4,059,457 | 11/1977 | Austin . |
| 4,062,921 | 12/1977 | Austin . |
| 4,464,389 | 8/1984 | Dawson . |
| 4,608,078 | 8/1986 | Acker et al. . |
| 4,873,092 | 10/1989 | Azuma et al. . |
| 5,204,107 | 4/1993 | Tsurutani et al. . |
| 5,242,932 * | 9/1993 | Gandy et al. ........................ 514/313 |
| 5,439,446 | 8/1995 | Barry . |
| 5,442,048 | 8/1995 | Meister et al. . |
| 5,510,418 | 4/1996 | Rhee et al. . |
| 5,532,221 | 7/1996 | Huang et al. . |
| 5,536,508 | 7/1996 | Canal et al. . |
| 5,580,575 | 12/1996 | Unger et al. . |
| 5,696,154 | 12/1997 | Malspeis et al. . |
| 5,744,155 | 4/1998 | Friedman et al. . |
| 5,747,475 | 5/1998 | Nordquist et al. . |
| 5,762,903 | 6/1998 | Park et al. . |
| 5,773,592 | 6/1998 | Mills . |
| 5,846,952 | 12/1998 | Vournakis et al. . |
| 5,871,710 | 2/1999 | Bogdanov et al. . |
| 5,874,402 * | 2/1999 | Singh et al. ........................... 514/2 |

FOREIGN PATENT DOCUMENTS

| | | |
|---|---|---|
| 9218116 * | 10/1992 | (WO) . |
| 9325225 * | 12/1993 | (WO) . |
| 9621438 * | 7/1996 | (WO) . |

* cited by examiner

*Primary Examiner*—William R. A. Jarvis
*Assistant Examiner*—Vickie Kim
(74) *Attorney, Agent, or Firm*—Mark A. Wilson; Reed & Associates

(57) ABSTRACT

Novel pharmaceutical formulations for treating a cellular proliferative disease are provided comprising: a therapeutically effective amount of a Golgi apparatus disturbing agent; a biocompatible carrier; and a solvent. In preferred formulations, the Golgi apparatus disturbing agent is brefeldin A (BFA) and the biocompatible carrier is a polymer such as chitin or chitosan. Methods of treating cellular proliferative diseases using the pharmaceutical formulations are also described.

20 Claims, 3 Drawing Sheets

(2 of 3 Drawing Sheet(s) Filed in Color)

TREATMENT OF ONCOLOGIC TUMORS WITH AN INJECTABLE FORMULATION OF A GOLGI APPARATUS DISTURBING AGENT

CROSS-REFERENCE TO RELATED APPLICATIONS

This application claims priority to provisional U.S. Patent Application Ser. No. 60/100,479 entitled "Treatment of Oncologic Tumors with a Sustained Release Composition of Brefeldin A and other Pharmacologically Active Agents" filed Sep. 16, 1998.

TECHNICAL FIELD

This invention relates to pharmaceutical formulations comprising pharmacologically active agents, biocompatible carriers, and solvents and the like. More particularly, the invention relates to pharmaceutical formulations containing Golgi apparatus disturbing agents such as, for example, brefeldin A. This invention also relates to methods of treating cellular proliferative diseases in patients in need of such therapy.

BACKGROUND

Local cancer chemotherapy involves the introduction of an anti-cancer agent near or within a tumor. As a potential cure for some cancers, local chemotherapy has generated a tremendous interest among researchers and health care providers, in part because local chemotherapy (in contrast to systemic delivery) avoids or minimizes the potential for systemic toxicity, and in part because the target site can be exposed to higher concentrations of the active agent than possible with conventional chemotherapy. Thus, local chemotherapy can provide a useful tool in the treatment of some cancers.

Local chemotherapy is not, however, without drawbacks. One problem associated with local chemotherapy is insufficient retention of the chemotherapeutic agent at the target site (i.e., the diseased organ or tissue). Another problem with local chemotherapy (and many types of chemotherapy, for that matter) is the insoluble or slightly soluble nature of the active agent. Thus, the ability of local chemotherapy to offer a cure for some cancers has been compromised by retention and/or solubility problems associated with previously known or suggested chemotherapeutic agents and formulations.

The proposed solutions to these problems either do not fully address these drawbacks or create their own additional drawbacks. One often-cited approach is to employ a sustained release delivery system of a pharmacologically active anti-cancer agent. It is believed that locally administered, sustained release delivery systems allow high doses of the anti-cancer agent to be delivered while ensuring sufficient retention at the target site. Theoretically, such an approach would both increase efficacy and limit toxicity. To date, however, such approaches have not been effective. Thus additional agents and formulations are needed in order to bring the full potential of local chemotherapy to fruition.

Recently, there has been a significant interest in Golgi apparatus disturbing agents, particularly brefeldin A, due to its reported anti-tumor activity. Brefeldin A (BFA) was first described to be an antifungal, cytotoxic, and cancerostatic antibiotic. Haerri, et al. (1963) *Chem. Abs.* 59:5726h. Brefeldin A was also reported to have anti-viral properties. Tamura et al. (1968) *J. Antibiotics* 21:161–166. In recent years, brefeldin A has been studied extensively as a protein transport inhibitor. It is believed that brefeldin A can reversibly disrupt the Golgi apparatus, thereby affecting protein transport through the cytoplasm. Domes et al. (1989) *J. Cell Biol.* 109:61–72 (1989); Lippincott-Schwartz et al. (1991) *J. Cell Biol.* 112:567–577. It is now known that brefeldin A induces retrograde membrane transport from Golgi to the endoplasmic reticulum (ER). Dinter et al.(1998) *Histochem. Cell Biol.* 109:571–590. Currently brefeldin A is primarily used as a tool by researchers to interfere with the processing and sorting of finished proteins in order to more fully understand protein trafficking.

Due to solubility and related toxicity problems of brefeldin A, it has not yet been used successfully as an active agent in a pharmaceutical formulation. U.S. Pat. No. 4,608,078 to Acker et al. reported preparation of derivatives of brefeldin A in order to overcome solubility problems, but these derivatives still exhibited toxicity and insufficient solubility. In 1997, preparation and antitumor activity of water-soluble derivatives of brefeldin A were disclosed in U.S. Pat. No. 5,696,154 to Malspeis et al. These derivatives were claimed to be suitable for intravenous delivery in animals and humans. However, these analogs have been tested only in vitro and in very small amounts, which may not produce desired therapeutic effects in vivo. Thus, there remains a need for pharmaceutical formulations which can deliver, inter alia, insoluble or slightly soluble active agents such as brefeldin A and other Golgi apparatus disturbing agents, for the treatment of cellular proliferative diseases. There is a further need for pharmaceutical formulations of brefeldin A.

SUMMARY OF THE INVENTION

Accordingly, it is a primary object of the invention to address the aforementioned needs in the art and provide a pharmaceutical formulation comprising a Golgi apparatus disturbing agent as will be described in detail herein.

It is another object of the invention to provide a pharmaceutical formulation comprising brefeldin A as will be described in detail herein.

It is yet another object of the invention to provide such a formulation which significantly reduces the drawbacks associated with other types of local chemotherapy.

It is still another object of the invention to provide such a formulation which provides for sustained release of the active agent.

It is yet another object of the invention to provide such a formulation which increases the solubility of an otherwise insoluble or slightly soluble active agent.

It is a further object of the invention to provide a method of treating a cellular proliferative disease comprising administering to a patient in need thereof the pharmaceutical formulation of the invention as described in detail herein.

Additional objects, advantages and novel features of the invention will be set forth in part in the description which follows, and in part will become apparent to those skilled in the art upon examination of the following, or may be learned by practice of the invention.

In a first embodiment, then, a pharmaceutical formulation for treating a cellular proliferative disease in a patient is provided comprising: a therapeutically effective amount of a Golgi apparatus disturbing agent; a biocompatible carrier; and a solvent.

The Golgi apparatus disturbing agent can be any agent known to interfere with the functioning of the Golgi apparatus but it is preferred that the Golgi disturbing apparatus disturbing agent is brefeldin A. The biocompatible carrier can comprise any substantially non-antigenic and non-toxic compound that can serve to increase the solubility of the active agent and/or provide a sustained release profile of the active agent following administration of the pharmaceutical formulation. Preferred carriers include polysaccharides and particularly preferred polysaccharides are selected from the group consisting of chitin, chitosan, and combinations thereof. It is preferred also that the biocompatible carrier is covalently linked to brefeldin A.

In another embodiment, a method of treating a cellular proliferative disease is provided comprising administering to a patient in need thereof a pharmaceutical formulation comprising: a therapeutically effective amount of a Golgi apparatus disturbing agent; a biocompatible carrier; and a solvent.

The method of treating includes injecting the pharmaceutical formulation directly or nearly directly to the target site (e.g., an area exhibiting cellular proliferative disease). Preferably, the method is useful for treating proliferative selected from the group consisting of brain cancer, bladder cancer, breast cancer, colorectal cancer, head and neck cancer, liver cancer, prostate cancer, and ovarian cancer.

BRIEF DESCRIPTION OF THE FIGURES

The file of this patent contains at least one drawing executed in color. Copies of the patent with color drawing(s) will be provided by the Patent & Trademark Office upon request and payment of the necessary fee.

DETAILED DESCRIPTION OF THE INVENTION

I. OVERVIEW AND DEFINITIONS

Figure 1:
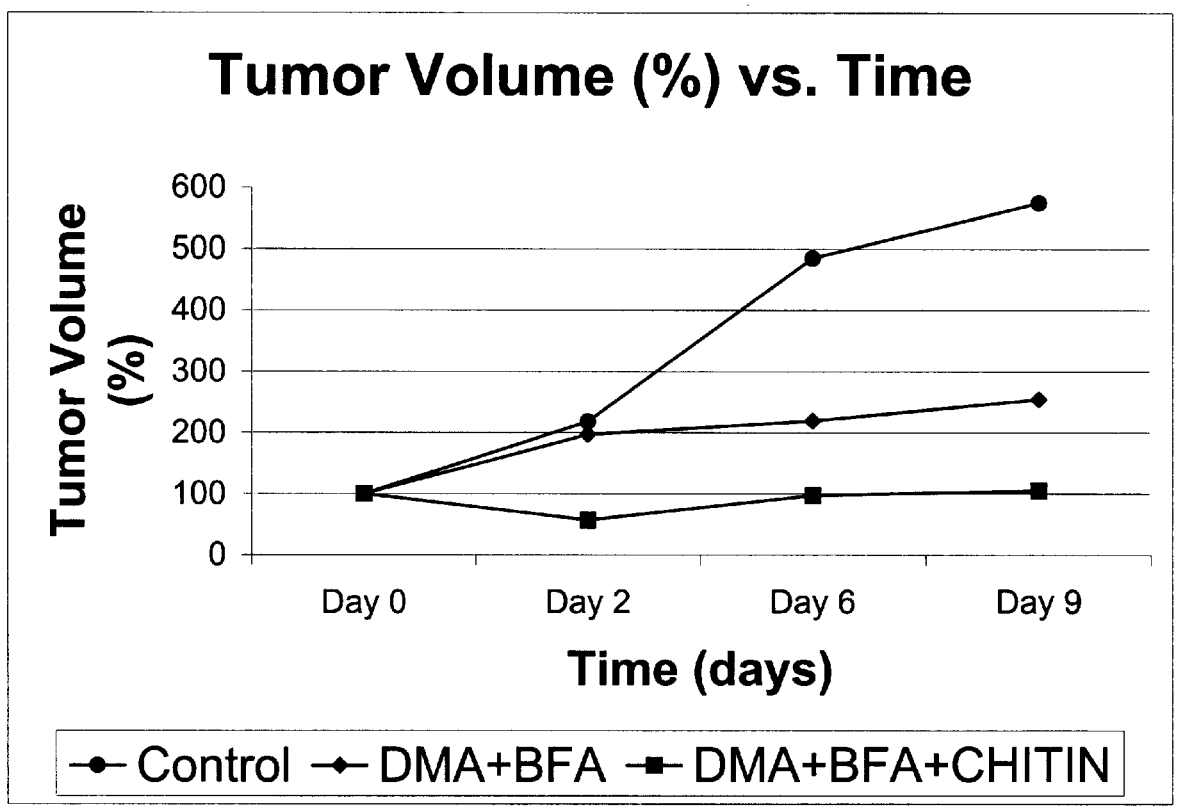
FIG. 1 is a graph depicting the change in tumor size with a brefeldin A formulation of the present invention, as evaluated in Example 1.

Before describing the present invention in detail, it is to be understood that unless otherwise indicated this invention is not limited to specific formulation components, manufacturing methods, dosage regimens, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to a "solvent"includes a combination of two or more solvents, etc.

In describing and claiming the present invention, the following terminology will be used in accordance with the definitions set forth below.

The terms "pharmacologically active agent," "active agent," and "drug" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect. The active agents herein are generally used in the treatment of cellular proliferative diseases.

The term "cellular proliferative disease" is intended to refer to any condition characterized by the undesired propagation of cells. Included are conditions such as neoplasms, cancers, and tumors. Also contemplated as "cellular proliferative diseases" are non-cancerous conditions such as benign melanomas and other cellular growths occurring within the epidermal layers.

The term "sustained release" as used herein refers to a drug formulation that provides for gradual release of drug over an extended period of time, and that preferably, although not necessarily, results in substantially constant levels at the desired site over an extended period of time.

"Vehicles" as used herein refer to materials suitable for drug administration. Vehicles useful herein include any such materials known in the art, e.g., any liquid, gel, solvent, liquid diluent, solubilizer, or the like, which is nontoxic and which does not interact with other components of the composition in a deleterious manner.

By the terms "effective amount" or "therapeutically effective amount"of an agent as provided herein are meant a sufficient amount of the agent to provide the desired therapeutic effect. Of course, undesirable effects (e.g., side effects) are sometimes manifested along with the desired therapeutic effect; hence a practitioner balances the potential benefits against the potential risks in determining what is an appropriate "therapeutically effective amount." As will be pointed out below, the exact amount required will vary from subject to subject, depending on the species, age, and general condition of the subject, mode of administration, and the like. Thus, it is not possible to specify an exact "effective amount." However, an appropriate "effective amount" in any individual case may be determined by one of ordinary skill in the art using only routine experimentation.

The terms "biocompatible" and "pharmacologically acceptable" as used herein are meant to refer to a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmacologically acceptable" salt or a "pharmacologically acceptable" ester of a compound as provided herein is a salt or ester which is not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" a cellular proliferative disease, as the term "treating" is used herein, encompasses both prevention of cellular proliferative diseases in a predisposed individual and treatment of cellular proliferative diseases in a clinically symptomatic individual.

"Optional" or "optionally" means that the subsequently described circumstance may or may not occur, so that the description includes instances where the circumstance occurs and instances where it does not.

"Patient" as used herein refers to a mammalian, preferably human individual who can benefit from the pharmaceutical formulations of the present invention. There is no limitation on the type of mammal which could benefit from the presently described pharmaceutical formulations.

II. THE PHARMACEUTICAL FORMULATION

In a first embodiment, the invention provides a pharmaceutical formulation for treating a cellular proliferative disease comprising: a therapeutically effective amount of a Golgi apparatus disturbing agent; a biocompatible carrier; and a solvent.

A. ACTIVE AGENT

It is particularly preferred that the active agent incorporated in the present invention is a Golgi apparatus disturbing agent. Golgi apparatus disturbing agents include those agents which can totally disrupt the entire Golgi network or simply block one of the protein trafficking pathways. Many Golgi apparatus disturbing agents are reversible, that is, once the agent is removed the Golgi apparatus functions normally. Although it is not entirely clear how Golgi apparatus disturbing agents interfere with the processing and sorting of finished proteins, more is known about the Golgi apparatus itself. The Golgi apparatus is found in all eukaryotic cells and is responsible for receiving the proteins from the endoplasmic reticulum. Once arriving at the Golgi apparatus the proteins can be modified and/or sorted for delivery to the required location within the cell. For example, the Golgi apparatus is responsible for adding sulfates to the amino acid tyrosine in certain proteins and cleaving various protein precursors to yield mature hormones and neurotransmitters to name but a few of its functions. Given the importance of the Golgi apparatus, it is clear how Golgi apparatus disturbing agents can serve as powerful and important therapeutic agents.

Although any Golgi apparatus disturbing agent can be included in the present invention, preferred Golgi apparatus disturbing agents include those selected from the group consisting of brefeldin A, nocodazole, ilimaquinone, bafilamycin, okadaic acid, retinoic acid and combinations thereof. Most preferred of the Golgi apparatus disturbing agents is brefeldin A.

Golgi apparatus disturbing agents (or any other active agent) may be present in the formulation as a salt, ester, amide, or other derivative, or may be functionalized in various ways as will be appreciated by those skilled in the art and as described in the pertinent texts, patents, and literature; however it is preferred that the formulation contain brefeldin A per se, i.e., not in its derivatived or functionalized form. The active agents of the present invention can either be synthesized using techniques well known in the art or obtained from commercial suppliers.

Golgi apparatus disturbing agents (or any other active agent incorporated into presently described pharmaceutical formulation) may exist in the formulation in the form of a salt, ester, amide, prodrug, derivative, or the like, provided the salt, ester, amide, prodrug or derivative is suitable pharmacologically, i.e., effective in treating its intended cellular proliferative disease. Salts, esters, amides, prodrugs and other derivatives of the active agents may be prepared using standard procedures known to those skilled in the art of synthetic organic chemistry and described, for example, by J. March, *Advanced Organic Chemistry: Reactions Mechanisms and Structure*, 4th Ed. (New York: Wiley-Interscience, 1992). For example, acid addition salts are prepared from the free base using conventional methodology, and involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of acid moieties which may be present on a active agent molecule are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., sodium salt, and copper salts. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

The amount of active agent in the formulation is preferably a unit dosage and is present in an amount of from about 0.01 mg to about 10 g. It is particularly preferred that the active agent is present in an amount of from about 0.1 mg to about 1000 mg. Most preferably, the active agent is present in an amount of from about 1 mg to about 100 mg.

When the active agent in the formulation is brefeldin A, the formulation is preferably a unit dosage formulation. In such a formulation, brefeldin A is preferably present in an amount of from about 0.01 mg to about 10 g. It is particularly preferred that brefeldin A is present in an amount of from about 0.1 mg to about 1000 mg. Most preferably, brefeldin A is present in an amount of from about 1 mg to about 100 mg.

B. BIOCOMPATIBLE CARRIER

The biocompatible carrier can comprise any substantially non-antigenic compound that can serve to increase the solubility of the active agent and/or provide a sustained release profile of the active agent following administration of the pharmaceutical formulation. Preferred carriers are selected from the group consisting of polysaccharides, salts of polysaccharides, microspheres of polysaccharides, dextrins, gums, celluloses, silicones, liposomes and combinations thereof It is particularly preferred that the biocompatible carrier is a polysaccharide. It is particularly preferred that the polysaccharide is selected from the group consisting of chitin (poly-N-acetyl-D-glucosamine), chitosan (deacetylated chitin), and combinations thereof Of course derivatives of these carriers are contemplated as well, including, for example, derivatives formed by adding or removing sugar molecules (i.e. by increasing or decreasing the weight average molecular weight of the carrier). Thus preferred carriers may have a weight average molecular weight of from about 500 daltons to about 100,000 daltons, more preferably between about 10,000 daltons and 60,000 daltons.

Optimally, the biocompatible carrier can be covalently bonded to the active agent producing a carrier-active agent conjugate. For example, chitin can be covalently bonded to brefeldin A, typically through the 1-OH or 13-OH moieties of the active agent. Other types of bonds (e.g, ionic, van der Waals, etc.) between the carrier and active agent are contemplated as well. Thus, in some embodiments of the present invention, it is preferred that the biocompatible polymer is covalently linked to brefeldin A. Methods of producing these conjugates are well known to those skilled in the art, and described in detail in the pertinent texts and literature.

The amount of the biocompatible carrier present in the formulation will vary depending on the particular active agent and carrier used. Of course, the amount of biocompatible carrier present will also depend on other factors, such as whether the formulation is intended to contain a single dose or multiple doses and the injectability (e.g., viscosity) of the resulting formulation. In addition the amount of the carrier should be considered in light of the target area's environment in which the pharmaceutical formulation will be administered. For example, it is desirable that low viscosity organs such as the prostate, brain or bladder receive a low viscosity formulation, while dense tissue exemplified by solid tumors and breast tumors should receive a high viscosity pharmaceutical formulation. These and other factors are routinely considered by those skilled in the art. Thus, the amount of biocompatible carrier to be included in the pharmaceutical formulation can be established by those skilled in the art without undue experimentation.

The amount of biocompatible carrier contained in the formulation is preferably present in an amount of from about 0.01% w/v to about 50% w/v of the total formulation. It is particularly preferred that the biocompatible carrier is present in an amount of from about 0.5% w/v to about 30% w/v. Most preferably, the biocompatible carrier is present in an amount of from about 1% w/v to about 20% w/v. When the carrier is chitin, chitosan, or a combination thereof, it is preferred that the carrier be present in an amount of from about 1% to about 20% w/v of the entire formulation.

C. SOLVENT

The Golgi apparatus disturbing agent and biocompatible carrier are present in a pharmaceutically acceptable solvent. The solvent may be aqueous.

Aqueous solvents include, for example, water, saline, liposomes, oil-in-water emulsions and the like. Alternatively, the solvent may be non-aqueous. Non-aqueous solvents include, for example, 1-butanol, 2-butanol, ethanol, ethyl ether, ethyl formate, ethyl acetate, methyl acetate, 3-methyl-1-butanol, isobutyl acetate, isopropyl acetate, 2-methyl-1-propanol, methylethyl ketone, dimethylacetamide (DMA), 1,1 -dimethyloxymethane, 2,2-dimethyloxypropane, propylene glycol and water-in-oil emulsions and the like. The solvent may be an organic solvent or an inorganic solvent. As will be readily appreciated by one skilled in the art, the choice of solvent will depend on the desired solubility, the nature of the agents comprising the formulation, and the desired release characteristics.

The amount of solvent present in the formulation will vary depending on the type of tumor (solid or soft), solubility of active agent, the solvent chosen, and desired form of the formulation (i.e. solution, suspension, etc.) involved. Of course, the amount of solvent present will also depend on other factors, such as whether the formulation is intended to contain a single dose or multiple doses. Such factors are routinely considered by those skilled in the art. Thus, the amount of solvent to be included in the pharmaceutical formulation can be established by those skilled in the art without undue experimentation.

The amount of solvent contained in the formulation is preferably present in an amount of from about 0.01% by volume to about 50% by volume (v/v) of formulation. It is particularly preferred that the solvent is present in an amount of from about 0.1% by volume to about 30% by volume of formulation. Most preferably, the solvent is present in an amount of from about 1% by volume to about 10% by volume of formulation. When the solvent used in the formulation is chosen from the group consisting of dimethylacetamide, 1,1 -dimethyloxymethane, 2,2-dimethyloxypropane, propylene glycol, and combinations thereof, it is preferred that the solvent is present in an amount of from about 0.1% by volume to about 5% by volume of the formulation.

D. DELIVERY FORMS AND ADDITIONAL COMPONENTS

The pharmaceutical formulations of the present invention can be any art-known form. A non-limiting list of preferred delivery forms of the present invention include solution, suspension, dispersion, emulsion, microspheres and similar formulations.

As will be readily appreciated by those skilled in the art, the Golgi apparatus disturbing agent incorporated in the present invention can be substituted for or added with any other class of active agent which interferes with cellular proliferation. Classes of active agents suitable for inclusion in the present invention (either alone or as an additional agent) include but are not limited to agents selected from the group consisting of agents causing apoptosis (cell death), agents preventing RNA synthesis, agents that interfere with protein transport, alkylating agents, anesthetic agents, anti-angiogenic agents, antibacterial agents, anti-bodies, anti-fungal agents, anti-metabolite agents, anti-neoplastic agents with known anti-proliferative activity, anti-tumor antibiotics, anti-viral agents, biologically active peptides, biologically active proteins, chemotherapeutic agents, chimeric peptides and proteins, cytokines, endostatin agents, fusion proteins, Golgi apparatus disturbing agents, interferons, monoclonal antibody-toxins, oligonucleotides, pain-relieving agents, plant alkaloids, signal transduction inhibitors, and signal transduction pathway inhibitors such as inhibitors of kinases and phosphatases and combinations thereof.

Specific examples of active agents which are suitable for inclusion in the present invention (either alone or as an additional agent) include but are not limited to agents selected from the group consisting of consisting of actinomycin-D, aldesleukin, aminoglutethimide, amsacrine, anastozole, L-asparaginase, 5-azacytidine, aziridinylbenzoquinone (AZQ), bafilamycin, bioallenthim, bleomycin, bicalutamide, brefeldin A, buserelin, busulfan, carboplatin, carmustine (BCNU), chlorambucil, cisplatin (cis-DDP), cladribine, colchicinefosfamide, cyclophosphamide, cyproterone, cytarabine (Ara-C), dacarbazine, dactinomycin, daunorubicin, deoxycoformycin, diethylstilbestrol, docetaxel, doxorubicin, doxycycline, epirubicin, estramustine, etoposide (VP-16), fludarabine, fludrocortisone, 5-fluorodeoxyuridine, 5-fluorouracil (5-FU), fluoxymesterone, flutamide, gemcitabine, genistein, goserelin, hydroxyurea, idarubicin, ifosfamide, ilimaquinone, α-interferon, irinotecan, leucovorin, leuprolide, levamisole, lomustine (CCNU), mechlorethamine, medroxyprogesterone, megestrol, melphalan, mercaptopurine (6-MP), mesna, methotrexate (MTX), minocycline, mithramycin, mitomycine, mitotane, mitoxantrone, nilutamide, nocodazole, okadaic acid, octreotide, paclitaxel, pentostatin, plicamycin, porfimer, procarbazine, retinoic acid, staurosporine, streptozocin, suramin, tamoxifen, tautomycin, teniposide (ETP), testolactone, 6-thioguanine (6-TG), thiotepa, topotecan, tyrphostins, vinblastine (VLB), vincristine (VCR), vindesine, vinorelbine, wortmannin, derivatives thereof and combinations thereof.

The pharmaceutical formulation may include one or more additional components. Additional components include, for example, anti-microbials, buffers, antioxidants, and tonicity agents. Anti-microbial agents are used to deter the growth of microorganisms, particularly in multiple dose formulations (i.e. formulation for a multiple dose vial). Suitable anti-microbial agents include, phenylmercuric nitrate, thimerosal, benzethonium chloride, benzalkonium chloride, phenol, cresol, chlorobutanol, and combinations thereof. Buffers are used primarily to stabilize a solution against potential chemical degradation resulting from a change in the formulation's pH. Suitable buffers include acid salts of citrates, acetates, and phosphates. Antioxidants are used to preserve products because of the ease with which drugs may oxidize. Examples of antioxidants include sodium bisulfite, acetone sodium bisulfite, sodium formaldehyde, sulfoxylate, and thiourea, sodium salt of ethylenediaminetetraacetic acid, and substitution with an inert gas (e.g, nitrogen). Tonicity agents are used to control tonicity to enure that the resulting formulation is not excessively hypotonic or hypertonic relative to the physiological state. Examples of tonicity agents include electrolytes (e.g. sodium chloride), and mono- or disaccharides (e.g., dextrose for monosaccharides).

The amount of additional components which are not active agents will vary depending on the solvents chosen, desired form of the formulation and other factors. Such factors are routinely considered by those skilled in the art. Thus the amount of additional components which are not active agents can be established by those skilled in the art without undue experimentation.

The amount of such components preferably will not exceed 10% by volume of the total formulation. More preferably such components will not exceed 1% by volume of the total formulation. Most preferably such components will be present in an amount of from about 0.001% by volume to about 1.0%.

E. PHARMACOKINETIC PROFILE

The pharmaceutical formulations of the present invention are preferably sustained release formulations. That is, the formulation releases the active agent over an extended period of time relative to an immediate release or non-sustained release formulation. It is preferred that the pharmaceutical formulations of the present invention release active agent over a time of from about 4 hours to about 24 hours.

III. METHODS OF TREATMENT

The present invention also provides a method of treating a cellular proliferative disease comprising administering to a patient in need thereof a pharmaceutical formulation comprising: a therapeutically effective amount of a Golgi apparatus disturbing agent; a biocompatible carrier; and a solvent.

It is preferred that the method of administering the pharmaceutical formulation to the patient is via local injection. Those skilled in the art will recognize that delivery via injection contemplates the use of a syringe, catheter or similar device, which delivers the pharmaceutical formulation of the invention to the target site, i.e., to an area exhibiting cellular proliferative disease. Delivery may be direct, i.e., intratumoral, or nearly direct, i.e., intralesional, that is, to an area that is sufficiently close to a tumor so that the active agent exhibits the desired pharmacological activity with respect to the tumor itself. Thus, the pharmaceutical formulations are preferably delivered intralesionally or intratumorally. In addition, it is preferred that the patient is human. It is also preferred that the patient is a mammal.

The amount of the active agent administered will, of course, be dependent on the subject being treated, the subject's weight, the manner of administration and the judgement of the prescribing physician. In the method of the invention, i.e., preventing or treating a cellular proliferative disease, an initial dosing schedule will generally involve administering doses of from about 0.01 mg/kg to about 10 g/kg of the patient's body weight. It is particularly preferred that the active agent is administered in an amount of from about 0.1 mg/kg to about 1000 mg/kg of the patient's body weight. Most preferably, the active agent is administered in an amount of from about 1 mg/kg to about 100 mg/kg of the patient's body weight. Depending on the response of the disease, additional dosages within this range can be administered in order to treat the disease.

The total amount of the formulation delivered to the diseased site will depend on, inter alia, the size, extent and type of tumor and the patient's body weight. Generally, it is preferred that the total volume administered is between about 0.1 mL to about 60 mL and more preferably between about 0.5 mL to about 30 mL. Most preferably, the total volume administered of the presently described pharmaceutical formulation is from about 1.0 mL to about 15 mL.

It is preferred that the pharmaceutical formulations of the present invention be directed to the target area with the assistance of a CT, ultrasound, or similar device in order to ensure correct placement. Once the initial dose is administered, the patient may be given other doses either immediately or after a period of time. Such a dosing schedule can easily be determined by one skilled in the art after taking into consideration the nature of the disease, strength of the patient, expected effects of the formulation, etc.

It is intended that by local delivery of the presently described pharmaceutical formulation, higher concentration of the active agent can be retained at the target site. There are several advantages to having high concentrations delivered directly at the target site. First, since the active agent is localized, there is less potential for toxicity to the patient since little systemic circulation occurs. Second, drug efficacy is improved since the target site is exposed to higher concentrations of drug. Third, the relatively fast delivery ensures both solubility of the drug and little or no degradation of the active agent before reaching the target site. Fourth, the method is non-invasive, which is ideal for unresectable tumors such as brain tumors, liver tumors, and pancreatic tumors.

The cellular proliferative disease that can be treated using the present methods and formulations will, of course, depend on the active agent which is incorporated into the pharmaceutical formulation. Generally speaking, cellular proliferative diseases comprise all sarcomas, carcinomas, lymphomas, and malignant melanomas but also include, for example, non-cancerous melanomas and other benign growths caused by rapidly dividing cells.

Non-limiting examples of cellular proliferative diseases for which the present invention is suited include adrenocorticol cancer, bladder cancer, bone cancer, brain cancer, breast cancer, cervical cancer, colon cancer, colorectal cancer, endometrial cancer, esophogeal cancer, eye cancer, gallbladder cancer, gastric cancer, head and neck cancer, laryngeal cancer, liver cancer, lung cancer, melanoma, myeloproliferative disorders, neck cancer, nonmelanoma skin cancer, ovarian cancer, prostate cancer, pancreatic cancer, rectal cancer, and testicular cancer. Diseases for which the present invention is particularly well suited to treat and are therefore preferred include those diseases selected from the group consisting of brain cancer, bladder cancer, breast cancer, colon cancer, colorectal cancer, rectal cancer, head and neck cancer, liver cancer, prostate cancer and ovarian cancer.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will become apparent to those skilled in the art to which the invention pertains.

All patents, patent applications, and publications mentioned herein, both supra and infra are hereby incorporated herein by reference.

EXPERIMENTAL

For each of the following examples, the pharmaceutical formulations were prepared just prior to use. Various amounts of brefeldin A (mg of drug/kg animal's body weight) were weighed out and varying amounts of solvent was used to mix the drug. The mixtures were either vortexed (mechanical mixing) or sonicated until drug was either completely soluble or only a very small amount appeared to settle in the bottom the test tube. Chitin was then added and the mixture was sonicated.

In vivo activity was determined using nude mice carrying a human tumor. The human oral epithelial (KB-1) cells were kept in $CO_2/O_2$ atmosphere at 37 ° C., the cells were grown in monolayers, when confluent, cells were rinsed with ice cold phosphate buffered/EDTA, followed by Trypsin/EDTA treatment for about 3 minutes at 37 ° C. The cells were then dispersed by the addition of media with serum and spun down using a centrifuge and washed once in Phosphate Buffered Saline (PBS), prior to suspending at the desired density ($1 \times 10^7$ cells/mL) in sterile Hanks Balance Salt Solution (HBSS). The cells were then inoculated with a 100 ul injection on to each flank of the mice to provide $1 \times 10^6$ cells per site.

Six days following inoculation, the mice normally grew a tumor on each flank, ranging in size from 100 to 120 $mm^3$. The mice (average weight=25 g) were randomized and separated into groups. Each tumor was then measured and the tumor volume calculated and recorded. In experimental groups, one tumor on each mouse was treated with the appropriate agent (drug versus drug in formulation) with an injection volume of 50 ul using a 22G1/2 needle. The control group was left untreated.

Antitumor activity was determined by inhibition of tumor growth and survival rate. Each tumor was measured two to three times per week. In nude mice, tumors were measured for 10 days or until mice survived. In Balb/C tumors were measured for up to 20 days following treatment. The volume of the tumor was calculated and recorded. Tumor volume data is analyzed by using simple regression model.

EXAMPLE 1

In Vivo Efficacy of BFA, Chitin and Dimethylacetamide (DNA) in Nude Mice Carrying Human Epithelial (KB-1) Tumors Nude mice were divided into groups and given treatments according to Table 1.

TABLE 1

| Grp. | Treatment | # of treatments | Dose | # of tumors | Lethal toxicity |
|---|---|---|---|---|---|
| 1 | Untreated | — | —, —, — | 6 | 0 |
| 2 | DMA/BFA | 1 | 25 µl, 0.5 mg, | 4 | 0 |
| 3 | DMA/BFA/Chitin | 1 | 25 µl, 0.5 mg, 1 mg | 4 | 0 |

Results:

A higher degree of efficacy was demonstrated when brefeldin A was delivered with dimethylacetamide (DMA) and chitin (poly-N-acetyl-D-glucosamine), as compared to brefeldin A (BFA) with DMA. This three component formulation was extremely effective in tumor control: an acute response of blackening and almost total elimination of the tumor with one treatment of both BFA/DMA and BFA/DMA/chitin was observed. However, this response was more prominent in the sustained formulation (i.e., BFA/DMA/Chitin).

The following results were obtained. Vol represents the average tumor volume in $mm^3$ in a given group. % represents the normalized tumor volume from day 0.

| Group | Day 0 Vol. | Day 0 % | Day 2 Vol. | Day 2 % | Day 6 Vol. | Day 6 % | Day 9 Vol. | Day 9 % |
|---|---|---|---|---|---|---|---|---|
| Control | 83.7 | 100.0 | 182.3 | 217.8 | 405.9 | 484.9 | 481.0 | 574.7 |
| DMA + BFA | 49.1 | 100.0 | 96.9 | 197.4 | 107.5 | 218.9 | 125.1 | 254.8 |
| DMA + BFA + Chitin | 152.0 | 100.0 | 86.2 | 56.7 | 147.9 | 97.3 | 159.1 | 104.7 |

A graph as seen in FIG. 1 depicts the change in tumor size with a control and a sustained release formulation of brefeldin A. Not only were the brefeldin A formulations useful in treating the tumor, they were effective as well.

Figure 2A:
FIGS. 2a and 2b are color photographs of treated and untreated mice at day 0 and at day 2 as evaluated in Example 1.
Figure 2A:
Figure 2B:
Figure 2B:

As seen in the top photographs in FIGS. 2a and 2b all mice at day 0 exhibited intradermal human epithelial (KB-1) tumors.

As seen in the bottom photograph of FIG. 2b mice which were treated with brefeldin A, chitin and DMA showed dramatic improvement within 48 hours in their lesions than the mice which were untreated (bottom photograph of FIG. 2b). Thus, in vivo efficacy was established.

EXAMPLE 2

In vivo Efficacy of Brefeldin A, Chitin and Varying Amount of Dimethylacetamide (DMA) in Balb/C Mice Carrying Erlich Tumors Balb/C mice are divided into groups and given treatments according to Table 2.

TABLE 2

| Grp. | Treatment | # of treatments | Dose | # of tumor | Lethal toxicity | T/C |
|---|---|---|---|---|---|---|
| 1 | Untreated | — | —, —, — | 6 | 0 | — |
| 2 | DMA | 1 | 20 µl, —, — | 6 | 0 | 1.20 |
| 3 | DMA | 1 | 10 µl, —, — | 6 | 0 | 1.15 |
| 4 | DMA | 1 | 5 µl, —, — | 6 | 0 | 1.10 |
| 5 | DMA/BFA | 1 | 20 µl, 0.5 mg, | 6 | 0 | 1.75 |

TABLE 2-continued

| Grp. | Treatment | # of treatments | Dose | # of tumor | Lethal toxicity | T/C |
|---|---|---|---|---|---|---|
| 6 | DMA/BFA | 1 | 10 µl, 0.5 mg, — | 6 | 0 | 1.40 |
| 7 | DMA/BFA | 1 | 5 µl, 0.5 mg, — | 6 | 0 | 1.25 |
| 8 | DMA/BFA/Chitin | 1 | 20 µl, 0.5 mg, 1 mg | 6 | 0 | 2.75 |
| 9 | DMA/BFA/Chitin | 1 | 10 µl, 0.5 mg, 1 mg | 6 | 0 | 2.50 |
| 10 | DMA/BFA/Chitin | 1 | 5 µl, 0.5 mg, 1 mg | 6 | 0 | 2.00 |

T/C: ratio of delay in tumor growth in response to treatment (T) vs. untreated control (C).

Results:

A high T/C ratio (2.00–2.75) of delay in tumor growth for groups 8, 9, and 10 demonstrates a significant increase in the efficacy of brefeldin A when delivered with DMA and chitin.

In groups 5, 6, and 7, where brefeldin A is given with the solvent, a lower T/C ratio (1.25–1.75) is obtained and even lower T/C ratios (1.10–1.20) are obtained in groups 2, 3, and 4, where mice are treated with different amounts of DMA.

EXAMPLE 3

Survival of Balb/C Mice Following Treatment with Brefeldin A, DMA, and Chitin, Separately and in Combination Balb/C mice are divided into groups and given treatments according to Table 3. Mice are observed daily for 25 days for deaths due to toxicity.

TABLE 3

| Grp. | Treatment | # of treatments | Dose | # of tumors | # of Deaths |
|---|---|---|---|---|---|
| 1 | Untreated | — | —, —, — | 10 | 0 |
| 2 | DMA/_/_ | 1 | 30 µl, —, — | 10 | 2 |
| 3 | DMA/_/Chitin | 1 | 30 µl, —, 1 mg | 10 | 0 |
| 4 | DMA/BFA/_ | 1 | 30 µl, 2 mg, — | 10 | 4 |
| 5 | DMA/BFA/Chitin | 1 | 30 µl, 2 mg, 1 mg | 10 | 1 |
| 6 | DMA/_/_ | 1 | 10 µl, —, — | 10 | 0 |
| 7 | DMA/_/Chitin | 1 | 10 µl, —, 1 mg | 10 | 0 |
| 8 | DMA/BFA/_ | 1 | 10 µl, 1 mg, — | 10 | 2 |
| 9 | DMA/BFA/Chitin | 1 | 10 µl, 1 mg, 1 mg | 10 | 0 |

Results:

Administration of high doses of brefeldin (80 mg/kg and 40 mg/kg) with DMA (80% and 20%) in groups 4 and 8, are proved to be most toxic to mice. However, when chitin is added to the formulation, less toxicity to mice is observed, most likely due to the sustained release effect.

EXAMPLE 4

In Vivo Efficacy of Brefeldin A, DMA with Varying Amount of Chitin in Balb/C Mice Carrying Erlich Tumors Balb/C mice are divided into groups and given treatments according to Table 4. Mice are observed daily to evaluate lethal toxicity and tumors are measured on alternate days for 20 days.

TABLE 4

| Grp. | Treatment | # of treatments | Dose | # of tumor | Lethal toxicity | T/C |
|---|---|---|---|---|---|---|
| 1 | Untreated | — | —, —, — | 6 | 0 | — |
| 2 | DMA | 1 | 10 µl, —, — | 6 | 0 | 1.17 |
| 3 | DMA/BFA/_ | 1 | 10 µl, 2 mg, — | 6 | 1 | 2.50 |
| 4 | DMA/BFA/Chitin | 1 | 10 µl, 2 mg, 1 mg | 6 | 0 | 2.85 |
| 5 | DMA/BFA/Chitin | 1 | 10 µl, 2 mg, 0.5 mg | 6 | 1 | 2.77 |
| 6 | DMA/BFA/Chitin | 1 | 10 µl, 2 mg, 0.25 mg | 6 | 1 | 2.55 |
| 7 | DMA/BFA/Chitin | 1 | 10 µl, 0.5 mg, 1 mg | 6 | 0 | 2.55 |
| 8 | DMA/BFA/Chitin | 1 | 10 µl, 0.5 mg, 0.5 mg | 6 | 0 | 2.40 |
| 9 | DMA/BFA/Chitin | 1 | 10 µl, 0.5 mg, 0.25 mg | 6 | 0 | 2.30 |

T/C: ratio of delay in tumor growth in response to treatment (T) vs. untreated control (C).

Results:

Toxic Effects are observed with high doses of brefeldin A when administered with DMA and low amounts of chitin (3, 5, and 6). However this toxicity lessens when 1.0% to 2.0% of chitin is included in the formulation, groups 4, 5, 8, and 9.

A high T/C ratio (2.50–2.85) of delay in tumor growth for groups 4, 5, and 6 demonstrates a significant increase in the efficacy of brefeldin A when delivered with DMA and chitin.

When the dose of brefeldin A is decreased, as in groups 7, 8, and 9, a 5 decrease in T/C ratio (2.30–2.55) is observed.

EXAMPLE 5

In vivo Efficacy of Brefeldin A with Chitin and Ethyl Acetate (Veh A.) and Tetrahydrofuran (Veh. B) in Balb/C Mice Carrying Erlich Tumors BalbIC mice are divided into groups and given treatments according to Table 5.

TABLE 5

| Grp. | Treatment | # of treatments | Dose | # of tumors | Lethal toxicity | T/C |
|---|---|---|---|---|---|---|
| 1 | Untreated | — | — | 6 | 0 | — |
| 2 | Vehicle A/_/_ | 1 | 5 µl, —, — | 6 | 0 | 1.10 |
| 3 | Veh. A/BFA/_ | 1 | 5 µl, 0.5 mg, — | 6 | 0 | 1.35 |
| 4 | Veh. A/BFA/Chitin | 1 | 5 µl, 0.5 mg, 1 mg | 6 | 0 | 1.58 |
| 5 | Vehicle B/_/_ | 1 | 5 µl, —, — | 6 | 0 | 1.08 |
| 6 | Veh. B/BFA/_ | 1 | 5 µl, 0.5 mg, — | 6 | 0 | 1.40 |
| 7 | Veh. B/BFA/Chitin | 1 | 5 µl, 0.5 mg, 1 mg | 6 | 0 | 1.88 |

T/C: ratio of delay in tumor growth in response to treatment (T) vs. untreated control (C).

Results:

Mice treated with the triple component formulation (i.e. groups 4 and 7) demonstrate significantly reduced tumor size than all other groups. No statistical difference is demonstrated between the solvents chosen.

EXAMPLE 6

In Vivo Efficacy of Brefeldin A with Chitin and Ethyl Acetate (Veh. A) in Single vs. Multiple Doses in Balb/C Mice Carrying Erlich Tumors Balb/C mice are divided into groups and given treatments according to Table 6. Multiple dose groups receive injection every day for 5 days.

TABLE 6

| Grp. | Treatment | # of treatments | Dose | # of tumors | Lethal toxicity | T/C |
|---|---|---|---|---|---|---|
| 1 | Untreated | — | _, _, _ | 6 | 0 | — |
| 2 | Veh. A/_/_ | 1 | 5 µl, _, _ | 6 | 0 | 1.08 |
| 3 | Veh. A/BFA/_ | 1 | 5 µl, 0.5 mg, _ | 6 | 0 | 1.37 |
| 4 | Veh. A/BFA/Chitin | 1 | 5 µl, 0.5 mg, 1 mg | 6 | 0 | 1.54 |
| 5 | Vehicle A/_/_ | 5 | 5 µl, _, _ | 6 | 1 | 1.20 |
| 6 | Veh. A/BFA/_ | 5 | 5 µl, 0.5 mg, _ | 6 | 2 | 1.45 |
| 7 | Veh. A/BFA/Chitin | 5 | 5 µl, 0.5 mg, 1 mg | 6 | 1 | 1.98 |

T/C: ratio of delay in tumor growth in response to treatment (T) vs. untreated control (C).

Results:

Toxicity is observed in groups 5, 6, and 7 with multiple doses. Mice treated with the triple component formulation (i.e. groups 4 and 7) demonstrate increased efficacy than all other groups within the same number of treatments. As between groups 4 and 7, the mice receiving (group 7) exhibit a statistically greater reduction in tumor volume than mice receiving a single treatment.

EXAMPLE 7

Survival of Balb/C Mice Following a Single Treatment with Ethyl Acetate (Veh. A), BFA/Ethyl Acetate and BFA/Ethyl Acetate/Chitin Single vs. Multiple Doses Balb/C mice are divided into groups and given treatments according to Table 7.

TABLE 7

| Grp. | Treatment | # of treatments | Dose | # of tumors | # of deaths |
|---|---|---|---|---|---|
| 1 | Untreated | — | _, _, _ | 10 | 0 |
| 2 | Vehicle A/_/_ | 1 | 5 µl, _, _ | 10 | 0 |
| 3 | Veh. A/BFA/_ | 1 | 5 µl, 0.25 mg, _ | 10 | 0 |
| 4 | Veh. A/BFA/Chitin | 1 | 5 µl, 0.25 mg, 1 mg | 10 | 0 |
| 5 | Vehicle A/_/_ | 5 | 5 µl, _, _ | 10 | 1 |
| 6 | Veh. A/BFA/_ | 5 | 5 µl, 0.05 mg, _ | 10 | 1 |
| 7 | Veh. A/BFA/Chitin | 5 | 5 µl, 0.05 mg, 1 mg | 10 | 0 |

Results:

Multiple doses of ethyl acetate in groups 5 and 6 result in deaths in each group. All other animals tolerate the treatment.

What is claimed is:

1. A method of treating a cellular proliferative disease comprising administering to a patient in need thereof a pharmaceutical formulation comprising:

a therapeutically effective amount of a Golgi apparatus disturbing agent as a main active agent;

a biocompatible carrier selected from the group consisting of polysaccharides, salts of polysaccharides, microspheres of polysaccharides, dextrins, gums, celluloses, silicones, and comabinations thereof; and a solvent, wherein the formulation is delivered to said patient via injection.

2. The method of claim 1, wherein the cellular proliferative disease is selected from the group consisting of adrenocorticol cancer, bladder cancer, bone cancer, brain cancer, breast cancer, cervical cancer, colon cancer, colorectal cancer, endometrial cancer, esophogeal cancer, eye cancer, gallbladder cancer, gastric cancer, head and neck cancer, laryngeal cancer, liver cancer, lung cancer, melanoma, myeloproliferative disorders, neck cancer, nonmelanoma skin cancer, ovarian cancer, prostate cancer, pancreatic cancer, rectal cancer, and testicular cancer.

3. The method of claim 2, wherein the cellular proliferative disease is selected from the group consisting of brain cancer, bladder cancer, breast cancer, colorectal cancer, head and neck cancer, liver cancer, prostate cancer, and ovarian cancer.

4. The method of claim 1, wherein the injection of the pharmaceutical formulation is delivered intratumorally.

5. The method of claim 1, wherein the injection of the pharmaceutical formulation is delivered intralesionially.

6. The method of claim 1, wherein the patient is human.

7. The method of clain 1, wherein the patient is a mamnmal.

8. The method of claim 1, wherein the Golgi apparatus disturbing agent is brefeldin A.

9. The method of claim 1, wherein the pharmaceutical formulation is in unit dosage form.

10. The method of claim 9, wherein the Golgi apparatus disturbing agent is present in an amount of from about 0.01 mg to about 10 g.

11. The method of claim 10, wherein the Golgi apparatus disturbing agent is brefeldin A.

12. The method of claim 1, wherein the biocompatible carrier is a polysaccharide.

13. The method of claim 12, wherein the polysaccharide is selected from the group consisting of chitin, chitosan, and combinations thereof.

14. The method of clain 1, wherein the biocompatible carrier is present in an amount of from about 0.01% w/v to about 50% w/v of the total formulation.

15. The method of claim 1, wherein the solvent is selected from the group consisting of dimethylacetamide, 1,1-dimethyloxymethane, 2,2-dimethyloxypropane, propylene glycol, and combinations thereof.

16. The method of claim 1, wherein the solvent is present in an amount of from about 0.01% by volume to about 50% by volume (v/v) of formulation.

17. The method of claim 1, wherein the biocompatible carrier is covalently linked to brefeldin A.

18. The method of claim 1, wherein the pharmaceutical formulation provides a sustained release prole in vivo.

19. The method of claim 1, wherein the pharmaceutical formulation is adminstered via injection with a syringe.

20. The method of claim 1, wherein the pharmaceutical formulation is adminstered via a catheter.

* * * * *